(12) United States Patent
Medina

(10) Patent No.: US 8,257,274 B2
(45) Date of Patent: Sep. 4, 2012

(54) MEDICAL SENSOR AND TECHNIQUE FOR USING THE SAME

(75) Inventor: Casey V. Medina, Westminister, CO (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 858 days.

(21) Appl. No.: 12/237,522

(22) Filed: Sep. 25, 2008

(65) Prior Publication Data

US 2010/0076337 A1    Mar. 25, 2010

(51) Int. Cl.
*A61B 5/00* (2006.01)

(52) U.S. Cl. .................................. 600/549; 600/344

(58) Field of Classification Search .................... 600/549
See application file for complete search history.

(56) References Cited

U.S. PATENT DOCUMENTS

| | | | |
|---|---|---|---|
| 4,025,733 A | 5/1977 | Klar et al. |
| 4,047,400 A | 9/1977 | Thorneburg |
| 4,462,116 A | 7/1984 | Sanzone et al. |
| 4,499,741 A | 2/1985 | Harris |
| 4,510,938 A | 4/1985 | Jobsis et al. |
| 4,570,638 A | 2/1986 | Stoddart et al. |
| 4,675,919 A | 6/1987 | Heine et al. |
| 4,739,757 A | 4/1988 | Edwards |
| 4,775,116 A | 10/1988 | Klein |
| 4,784,162 A | 11/1988 | Ricks et al. |
| 4,802,485 A | 2/1989 | Bowers et al. |
| 4,825,872 A | 5/1989 | Tan et al. |
| 4,825,879 A | 5/1989 | Tan et al. |
| 4,833,734 A | 5/1989 | Der Estephanian |
| 4,838,279 A | 6/1989 | Fore |
| 4,856,116 A | 8/1989 | Sullivan |
| 4,890,619 A | 1/1990 | Hatschek |
| 4,910,804 A | 3/1990 | Lidgren |
| 4,918,758 A | 4/1990 | Rendina |
| 4,930,888 A | 6/1990 | Feisleben et al. |
| 4,942,877 A | 7/1990 | Sakai et al. |
| 4,972,331 A | 11/1990 | Chance |
| 4,977,011 A | 12/1990 | Smith |
| 4,991,234 A | 2/1991 | Greenberg |
| 4,996,975 A | 3/1991 | Nakamura |
| 5,005,374 A | 4/1991 | Spitler et al. |
| 5,054,488 A | 10/1991 | Muz |
| 5,080,096 A | 1/1992 | Hooper et al. |
| 5,080,098 A | 1/1992 | Willett et al. |
| H1039 H | 4/1992 | Tripp, Jr. et al. |
| 5,111,817 A | 5/1992 | Clark et al. |
| 5,119,815 A | 6/1992 | Chance |
| 5,122,974 A | 6/1992 | Chance |
| 5,125,403 A | 6/1992 | Culp |
| 5,167,230 A | 12/1992 | Chance |
| 5,188,108 A | 2/1993 | Secker |

(Continued)

FOREIGN PATENT DOCUMENTS

CN    1306260    8/2001

(Continued)

*Primary Examiner* — Max Hindenburg
*Assistant Examiner* — Charles Becker
(74) *Attorney, Agent, or Firm* — Fletcher Yoder

(57) ABSTRACT

According to various embodiments, a hat-based or headband sensor assembly may provide an output to indicate when a patient's body temperature changes. The sensor assembly may include sensors and other features to alert healthcare providers when a temperature is outside of a desired range. The sensor assembly may include a medical sensor, such as a pulse oximetry sensor, and a temperature sensor.

19 Claims, 6 Drawing Sheets

U.S. PATENT DOCUMENTS

| | | |
|---|---|---|
| 5,191,891 A | 3/1993 | Righter |
| 5,209,230 A | 5/1993 | Swedlow et al. |
| 5,214,409 A | 5/1993 | Beigel |
| 5,217,012 A | 6/1993 | Young et al. |
| 5,217,013 A | 6/1993 | Lewis et al. |
| 5,241,300 A | 8/1993 | Buschmann |
| 5,246,003 A | 9/1993 | DeLonzor |
| 5,253,645 A | 10/1993 | Friedman et al. |
| 5,267,563 A | 12/1993 | Swedlow et al. |
| 5,267,567 A | 12/1993 | Aung et al. |
| 5,295,490 A | 3/1994 | Dodakian |
| 5,313,940 A | 5/1994 | Fuse et al. |
| 5,337,744 A | 8/1994 | Branigan |
| 5,348,008 A | 9/1994 | Bornn et al. |
| 5,353,798 A | 10/1994 | Sieben |
| 5,354,979 A | 10/1994 | Adelson et al. |
| 5,357,953 A | 10/1994 | Merrick et al. |
| 5,368,025 A | 11/1994 | Young et al. |
| 5,368,562 A | 11/1994 | Blomquist et al. |
| 5,383,874 A | 1/1995 | Jackson et al. |
| 5,392,777 A | 2/1995 | Swedlow et al. |
| 5,398,689 A | 3/1995 | Conner et al. |
| 5,400,267 A | 3/1995 | Denen et al. |
| 5,405,269 A | 4/1995 | Stupecky |
| 5,405,614 A | 4/1995 | D'Angelo et al. |
| 5,413,099 A | 5/1995 | Schmidt et al. |
| 5,413,101 A | 5/1995 | Sugiura |
| 5,413,102 A | 5/1995 | Schmidt et al. |
| 5,415,166 A | 5/1995 | Imran |
| 5,425,360 A | 6/1995 | Nelson |
| 5,431,170 A | 7/1995 | Mathews |
| 5,437,275 A | 8/1995 | Amundsen et al. |
| 5,437,634 A | 8/1995 | Amano |
| 5,444,254 A | 8/1995 | Thomson |
| 5,451,763 A | 9/1995 | Pickett et al. |
| 5,452,717 A | 9/1995 | Branigan et al. |
| 5,465,714 A | 11/1995 | Scheuing |
| 5,469,845 A | 11/1995 | DeLonzor et al. |
| 5,482,034 A | 1/1996 | Lewis et al. |
| 5,490,523 A | 2/1996 | Isaacson et al. |
| 5,528,519 A | 6/1996 | Ohkura et al. |
| 5,546,955 A | 8/1996 | Wilk |
| 5,551,423 A | 9/1996 | Sugiura |
| 5,562,718 A | 10/1996 | Palermo |
| 5,564,108 A | 10/1996 | Hunsaker et al. |
| 5,564,417 A | 10/1996 | Chance |
| 5,584,296 A | 12/1996 | Cui et al. |
| 5,592,408 A | 1/1997 | Keskin et al. |
| 5,596,987 A | 1/1997 | Chance |
| 5,617,865 A | 4/1997 | Palczewska et al. |
| 5,617,866 A | 4/1997 | Marian, Jr. |
| 5,627,323 A | 5/1997 | Stern |
| 5,634,466 A | 6/1997 | Gruner |
| 5,638,593 A | 6/1997 | Gerhardt et al. |
| 5,638,818 A | 6/1997 | Diab et al. |
| 5,640,953 A | 6/1997 | Bishop et al. |
| 5,645,440 A | 7/1997 | Tobler et al. |
| 5,645,586 A | 7/1997 | Meltzer |
| 5,646,416 A | 7/1997 | Van de Velde |
| 5,671,750 A | 9/1997 | Shinoda |
| 5,673,708 A | 10/1997 | Athanasiou et al. |
| 5,678,544 A | 10/1997 | DeLonzor et al. |
| 5,681,285 A | 10/1997 | Ford et al. |
| 5,683,434 A | 11/1997 | Archer |
| 5,697,363 A | 12/1997 | Hart |
| 5,697,367 A | 12/1997 | Lewis et al. |
| 5,701,894 A | 12/1997 | Cherry et al. |
| 5,706,820 A | 1/1998 | Hossack et al. |
| 5,732,475 A | 3/1998 | Sacks et al. |
| 5,738,612 A | 4/1998 | Tsuda |
| 5,743,856 A | 4/1998 | Oka et al. |
| 5,743,857 A | 4/1998 | Shinoda et al. |
| 5,752,913 A | 5/1998 | Oka |
| 5,752,920 A | 5/1998 | Ogura et al. |
| 5,758,644 A | 6/1998 | Diab et al. |
| 5,772,601 A | 6/1998 | Oka et al. |
| 5,776,058 A | 7/1998 | Levinson et al. |
| 5,776,071 A | 7/1998 | Inuaki et al. |
| 5,779,631 A | 7/1998 | Chance |
| 5,779,639 A | 7/1998 | Yeung |
| 5,782,757 A | 7/1998 | Diab et al. |
| 5,786,592 A | 7/1998 | Hök |
| 5,791,347 A | 8/1998 | Flaherty et al. |
| 5,791,348 A | 8/1998 | Aung et al. |
| 5,792,052 A | 8/1998 | Isaacson et al. |
| 5,792,058 A | 8/1998 | Young et al. |
| 5,797,841 A | 8/1998 | Delonzor et al. |
| 5,810,724 A | 9/1998 | Gronvall |
| 5,813,980 A | 9/1998 | Levinson et al. |
| 5,823,012 A | 10/1998 | Hacskaylo |
| 5,823,952 A | 10/1998 | Levinson et al. |
| 5,826,277 A | 10/1998 | McConville |
| 5,830,136 A | 11/1998 | Delonzor et al. |
| 5,830,137 A | 11/1998 | Scharf et al. |
| 5,830,148 A | 11/1998 | Inuaki et al. |
| 5,830,149 A | 11/1998 | Oka et al. |
| 5,833,602 A | 11/1998 | Osemwota |
| 5,836,887 A | 11/1998 | Oka et al. |
| 5,839,439 A | 11/1998 | Nierlich et al. |
| RE36,000 E | 12/1998 | Swedlow et al. |
| 5,842,981 A | 12/1998 | Larsen et al. |
| 5,842,982 A | 12/1998 | Mannheimer |
| 5,851,179 A | 12/1998 | Ritson et al. |
| 5,857,974 A | 1/1999 | Eberle et al. |
| 5,860,932 A | 1/1999 | Goto et al. |
| 5,860,957 A | 1/1999 | Jacobsen et al. |
| 5,868,133 A | 2/1999 | DeVries et al. |
| 5,870,626 A | 2/1999 | Lebeau |
| 5,872,713 A | 2/1999 | Douglas et al. |
| 5,873,821 A | 2/1999 | Chance et al. |
| 5,879,294 A | 3/1999 | Anderson et al. |
| 5,891,021 A | 4/1999 | Dillon et al. |
| 5,891,026 A | 4/1999 | Wang et al. |
| 5,895,359 A | 4/1999 | Peel |
| 5,902,235 A | 5/1999 | Lewis et al. |
| 5,906,581 A | 5/1999 | Tsuda |
| 5,913,819 A | 6/1999 | Taylor et al. |
| 5,916,154 A | 6/1999 | Hobbs et al. |
| 5,919,133 A | 7/1999 | Taylor et al. |
| 5,931,790 A | 8/1999 | Peel |
| 5,931,791 A | 8/1999 | Saltzstein et al. |
| 5,934,925 A | 8/1999 | Tobler et al. |
| 5,936,539 A | 8/1999 | Fuchs |
| 5,947,905 A | 9/1999 | Hadjicostis et al. |
| 5,954,053 A | 9/1999 | Chance et al. |
| 5,957,850 A | 9/1999 | Marian, Jr. et al. |
| 5,964,701 A | 10/1999 | Asada et al. |
| 5,980,464 A | 11/1999 | Tsuda |
| 5,983,129 A | 11/1999 | Cowan et al. |
| 5,987,343 A | 11/1999 | Kinast |
| 5,987,351 A | 11/1999 | Chance |
| 5,991,648 A | 11/1999 | Levin |
| 5,995,077 A | 11/1999 | Wilcox et al. |
| 5,995,855 A | 11/1999 | Kiani et al. |
| 5,995,856 A | 11/1999 | Mannheimer et al. |
| 5,995,857 A | 11/1999 | Toomim et al. |
| 6,007,492 A | 12/1999 | Goto et al. |
| 6,011,986 A | 1/2000 | Diab et al. |
| 6,022,320 A | 2/2000 | Ogura et al. |
| 6,027,453 A | 2/2000 | Miwa et al. |
| 6,030,351 A | 2/2000 | Schmidt et al. |
| 6,031,603 A | 2/2000 | Fine et al. |
| 6,036,651 A | 3/2000 | Inuaki et al. |
| 6,041,247 A | 3/2000 | Weckstrom et al. |
| 6,047,201 A | 4/2000 | Jackson |
| 6,047,203 A | 4/2000 | Sackner et al. |
| 6,049,958 A | 4/2000 | Eberle et al. |
| 6,050,951 A | 4/2000 | Friedman et al. |
| 6,052,619 A | 4/2000 | John |
| 6,073,038 A | 6/2000 | Wang et al. |
| 6,084,380 A | 7/2000 | Burton |
| 6,085,752 A | 7/2000 | Kehr et al. |
| 6,088,607 A | 7/2000 | Diab et al. |
| 6,106,780 A | 8/2000 | Douglas et al. |
| 6,112,107 A | 8/2000 | Hannula |
| 6,115,621 A | 9/2000 | Chin |
| 6,118,382 A | 9/2000 | Hibbs et al. |

| | | | |
|---|---|---|---|
| 6,126,614 A * | 10/2000 | Jenkins et al. ................ 600/549 | |
| 6,134,459 A | 10/2000 | Roberts et al. | |
| 6,144,868 A | 11/2000 | Parker | |
| 6,149,481 A | 11/2000 | Wang et al. | |
| 6,152,754 A | 11/2000 | Gerhardt et al. | |
| 6,154,667 A | 11/2000 | Miura et al. | |
| 6,162,188 A | 12/2000 | Barnea | |
| 6,165,173 A | 12/2000 | Kamdar et al. | |
| 6,171,258 B1 | 1/2001 | Karakasoglu et al. | |
| 6,173,196 B1 | 1/2001 | Delonzor et al. | |
| 6,179,786 B1 | 1/2001 | Young | |
| 6,181,959 B1 | 1/2001 | Schollermann et al. | |
| 6,184,521 B1 | 2/2001 | Coffin, IV et al. | |
| 6,186,953 B1 | 2/2001 | Narimatsu | |
| 6,186,954 B1 | 2/2001 | Narimatsu | |
| 6,190,325 B1 | 2/2001 | Narimatsu | |
| 6,196,974 B1 | 3/2001 | Miwa | |
| 6,198,952 B1 | 3/2001 | Miesel | |
| 6,199,550 B1 | 3/2001 | Wiesmann et al. | |
| 6,209,144 B1 | 4/2001 | Carter | |
| 6,216,021 B1 | 4/2001 | Franceschini et al. | |
| 6,223,063 B1 | 4/2001 | Chaiken et al. | |
| 6,241,680 B1 | 6/2001 | Miwa | |
| 6,248,083 B1 | 6/2001 | Smith et al. | |
| 6,251,076 B1 | 6/2001 | Hovland et al. | |
| 6,251,080 B1 | 6/2001 | Henkin et al. | |
| 6,251,081 B1 | 6/2001 | Narimatsu | |
| 6,251,113 B1 | 6/2001 | Appelbaum et al. | |
| 6,256,523 B1 | 7/2001 | Diab et al. | |
| 6,256,524 B1 | 7/2001 | Walker et al. | |
| 6,263,221 B1 | 7/2001 | Chance et al. | |
| 6,263,223 B1 | 7/2001 | Shepherd et al. | |
| 6,280,213 B1 | 8/2001 | Tobler et al. | |
| 6,282,450 B1 | 8/2001 | Hartlaub et al. | |
| 6,283,922 B1 | 9/2001 | Goto et al. | |
| 6,285,895 B1 | 9/2001 | Ristolainen et al. | |
| 6,306,076 B1 | 10/2001 | Gill | |
| 6,308,089 B1 | 10/2001 | von der Ruhr et al. | |
| 6,321,100 B1 | 11/2001 | Parker | |
| 6,322,516 B1 | 11/2001 | Masuda et al. | |
| 6,343,223 B1 | 1/2002 | Chin et al. | |
| 6,343,224 B1 | 1/2002 | Parker | |
| 6,346,886 B1 | 2/2002 | De La Huerga | |
| 6,349,228 B1 | 2/2002 | Kiani et al. | |
| 6,356,774 B1 | 3/2002 | Bernstein et al. | |
| 6,362,622 B1 | 3/2002 | Stauber et al. | |
| 6,368,282 B1 | 4/2002 | Oka et al. | |
| 6,370,411 B1 | 4/2002 | Osadchy et al. | |
| 6,377,829 B1 | 4/2002 | Al-Ali | |
| 6,381,480 B1 | 4/2002 | Stoddart et al. | |
| 6,381,481 B1 | 4/2002 | Levendowski et al. | |
| 6,385,486 B1 | 5/2002 | John et al. | |
| 6,385,821 B1 | 5/2002 | Modgil et al. | |
| 6,387,092 B1 | 5/2002 | Burnside et al. | |
| 6,388,240 B2 | 5/2002 | Schulz et al. | |
| 6,397,091 B2 | 5/2002 | Diab et al. | |
| 6,405,075 B1 | 6/2002 | Levin | |
| 6,416,471 B1 | 7/2002 | Kumar et al. | |
| 6,416,474 B1 | 7/2002 | Penner et al. | |
| 6,417,774 B1 | 7/2002 | Hibbs et al. | |
| 6,423,010 B1 | 7/2002 | Friedman et al. | |
| 6,430,423 B2 | 8/2002 | DeLonzor et al. | |
| 6,432,050 B1 | 8/2002 | Porat et al. | |
| 6,450,168 B1 | 9/2002 | Nguyen | |
| 6,450,957 B1 | 9/2002 | Yoshimi et al. | |
| 6,450,981 B1 | 9/2002 | Shabty et al. | |
| 6,454,708 B1 | 9/2002 | Ferguson et al. | |
| 6,461,305 B1 | 10/2002 | Schnall | |
| 6,463,310 B1 | 10/2002 | Swedlow et al. | |
| 6,466,809 B1 | 10/2002 | Riley | |
| 6,468,241 B1 | 10/2002 | Gelfand et al. | |
| 6,470,199 B1 | 10/2002 | Kopotic et al. | |
| 6,470,279 B1 | 10/2002 | Samsoondar | |
| 6,480,762 B1 | 11/2002 | Uchikubo et al. | |
| 6,491,638 B2 | 12/2002 | Oka | |
| 6,491,639 B1 | 12/2002 | Turcott | |
| 6,503,087 B1 | 1/2003 | Eggert et al. | |
| 6,503,204 B1 | 1/2003 | Sumanaweera et al. | |
| 6,505,061 B2 | 1/2003 | Larson | |
| 6,511,478 B1 | 1/2003 | Burnside et al. |
| 6,516,289 B1 | 2/2003 | David |
| 6,519,487 B1 | 2/2003 | Parker |
| 6,524,257 B2 | 2/2003 | Ogura |
| 6,525,386 B1 | 2/2003 | Mills et al. |
| 6,526,309 B1 | 2/2003 | Chance |
| 6,526,970 B2 | 3/2003 | DeVries et al. |
| 6,527,725 B1 | 3/2003 | Inuaki et al. |
| 6,527,726 B2 | 3/2003 | Goto et al. |
| 6,535,765 B1 | 3/2003 | Amely-Velez et al. |
| 6,537,220 B1 | 3/2003 | Friemel et al. |
| 6,541,756 B2 | 4/2003 | Schulz et al. |
| 6,542,081 B2 | 4/2003 | Torch |
| 6,547,742 B2 | 4/2003 | Oka et al. |
| 6,547,743 B2 | 4/2003 | Brydon |
| 6,551,252 B2 | 4/2003 | Sackner et al. |
| 6,553,242 B1 | 4/2003 | Sarussi |
| 6,575,902 B1 | 6/2003 | Burton |
| 6,575,904 B2 | 6/2003 | Nagai et al. |
| 6,580,086 B1 | 6/2003 | Schulz et al. |
| 6,582,371 B2 | 6/2003 | Miller |
| 6,582,374 B2 | 6/2003 | Yokozeki |
| 6,584,356 B2 | 6/2003 | Wassmund et al. |
| 6,589,171 B2 | 7/2003 | Keirsbilck |
| 6,589,183 B2 | 7/2003 | Yokozeki |
| 6,589,189 B2 | 7/2003 | Meyerson et al. |
| 6,594,513 B1 | 7/2003 | Jobsis et al. |
| 6,597,933 B2 | 7/2003 | Kiani et al. |
| 6,605,038 B1 | 8/2003 | Teller et al. |
| 6,606,993 B1 | 8/2003 | Wiesmann et al. |
| 6,611,793 B1 | 8/2003 | Burnside et al. |
| 6,615,065 B1 | 9/2003 | Barrett et al. |
| 6,622,034 B1 | 9/2003 | Gorski et al. |
| 6,635,048 B1 | 10/2003 | Ullestad et al. |
| 6,640,116 B2 | 10/2003 | Diab |
| 6,645,154 B2 | 11/2003 | Oka |
| 6,645,155 B2 | 11/2003 | Inuaki et al. |
| 6,653,557 B2 | 11/2003 | Wolf et al. |
| 6,654,622 B1 | 11/2003 | Eberhard et al. |
| 6,662,033 B2 | 12/2003 | Casciani et al. |
| 6,666,860 B1 | 12/2003 | Takahashi |
| 6,671,531 B2 | 12/2003 | Al-Ali et al. |
| 6,671,545 B2 | 12/2003 | Fincke |
| 6,678,543 B2 | 1/2004 | Diab et al. |
| 6,681,454 B2 | 1/2004 | Modgil et al. |
| 6,684,091 B2 | 1/2004 | Parker |
| 6,694,160 B2 | 2/2004 | Chin |
| 6,695,806 B2 | 2/2004 | Gelfand et al. |
| 6,700,497 B2 | 3/2004 | Hibbs et al. |
| 6,704,601 B1 | 3/2004 | Amely-Velez et al. |
| 6,708,048 B1 | 3/2004 | Chance |
| 6,711,425 B1 | 3/2004 | Reuss |
| 6,712,767 B2 | 3/2004 | Hossack et al. |
| 6,721,585 B1 | 4/2004 | Parker |
| 6,721,602 B2 | 4/2004 | Engmark et al. |
| 6,725,075 B2 | 4/2004 | Al-Ali |
| 6,726,327 B2 | 4/2004 | Torrey et al. |
| 6,731,963 B2 | 5/2004 | Finarov et al. |
| 6,735,459 B2 | 5/2004 | Parker |
| 6,736,759 B1 | 5/2004 | Stubbs et al. |
| 6,736,786 B1 | 5/2004 | Shabty et al. |
| 6,743,173 B2 | 6/2004 | Penner et al. |
| 6,743,202 B2 | 6/2004 | Hirschman et al. |
| 6,745,061 B1 | 6/2004 | Hicks et al. |
| 6,748,254 B2 | 6/2004 | O'Neil et al. |
| 6,748,262 B2 | 6/2004 | Harada et al. |
| 6,749,567 B2 | 6/2004 | Davis |
| 6,755,789 B2 | 6/2004 | Stringer et al. |
| 6,758,808 B2 | 7/2004 | Paul |
| 6,763,255 B2 | 7/2004 | Delonzor et al. |
| 6,767,330 B2 | 7/2004 | Lavery |
| 6,771,994 B2 | 8/2004 | Kiani et al. |
| 6,776,758 B2 | 8/2004 | Peszynski et al. |
| 6,779,257 B2 | 8/2004 | Kiepen et al. |
| 6,785,568 B2 | 8/2004 | Chance |
| 6,792,300 B1 | 9/2004 | Diab et al. |
| 6,796,946 B2 | 9/2004 | Ogura et al. |
| 6,801,799 B2 | 10/2004 | Mendelson |
| 6,804,543 B2 | 10/2004 | Miller et al. |

| Patent No. | Date | Inventor |
|---|---|---|
| 6,804,558 B2 | 10/2004 | Haller et al. |
| 6,808,496 B2 | 10/2004 | Oka et al. |
| 6,811,538 B2 | 11/2004 | Westbrook et al. |
| 6,813,511 B2 | 11/2004 | Diab et al. |
| 6,816,741 B2 | 11/2004 | Diab et al. |
| 6,824,520 B2 | 11/2004 | Orr et al. |
| 6,827,688 B2 | 12/2004 | Goto et al. |
| 6,829,003 B2 | 12/2004 | Takami |
| 6,830,711 B2 | 12/2004 | Mills et al. |
| 6,832,987 B2 | 12/2004 | David et al. |
| 6,842,722 B2 | 1/2005 | David |
| 6,847,294 B1 | 1/2005 | Lin et al. |
| 6,849,074 B2 | 2/2005 | Chen et al. |
| 6,853,304 B2 | 2/2005 | Reisman et al. |
| 6,870,479 B2 | 3/2005 | Gabriel |
| 6,875,176 B2 | 4/2005 | Mourad et al. |
| 6,877,511 B2 | 4/2005 | DeVries et al. |
| 6,893,400 B2 | 5/2005 | Kawaguchi et al. |
| 6,898,299 B1 | 5/2005 | Brooks |
| 6,899,682 B2 | 5/2005 | Eberle et al. |
| 6,899,684 B2 | 5/2005 | Mault et al. |
| 6,904,124 B2 | 6/2005 | Staver et al. |
| 6,907,284 B2 | 6/2005 | Hamilton et al. |
| 6,909,912 B2 | 6/2005 | Melker |
| 6,911,027 B1 | 6/2005 | Edwards et al. |
| 6,915,167 B2 | 7/2005 | Splett et al. |
| 6,920,345 B2 | 7/2005 | Al-Ali et al. |
| 6,921,198 B2 | 7/2005 | Gruszecki et al. |
| 6,923,771 B2 | 8/2005 | Ogura et al. |
| 6,923,776 B2 | 8/2005 | Shabty et al. |
| 6,930,608 B2 | 8/2005 | Grajales et al. |
| 6,934,570 B2 | 8/2005 | Kiani et al. |
| 6,934,571 B2 | 8/2005 | Wiesmann et al. |
| 6,936,011 B2 | 8/2005 | Sheldon |
| 6,938,488 B2 | 9/2005 | Diaz et al. |
| 6,939,314 B2 | 9/2005 | Hall et al. |
| 6,943,881 B2 | 9/2005 | Wang |
| 6,944,498 B2 | 9/2005 | Owens et al. |
| 6,952,870 B2 | 10/2005 | Miller |
| 6,955,650 B2 | 10/2005 | Mault et al. |
| 6,965,071 B2 | 11/2005 | Watchko et al. |
| 6,971,790 B2 | 12/2005 | Quinn et al. |
| 6,979,329 B2 | 12/2005 | Burnside et al. |
| 6,985,763 B2 | 1/2006 | Boas et al. |
| 6,985,764 B2 | 1/2006 | Mason et al. |
| 6,990,371 B2 | 1/2006 | Powers et al. |
| 6,993,371 B2 | 1/2006 | Kiani et al. |
| 6,995,665 B2 | 2/2006 | Appelt et al. |
| 7,001,334 B2 | 2/2006 | Reed et al. |
| 7,017,420 B2 | 3/2006 | Kalvesten et al. |
| 7,018,338 B2 | 3/2006 | Vetter et al. |
| 7,019,392 B2 | 3/2006 | Iwasaki |
| 7,020,508 B2 | 3/2006 | Stivoric et al. |
| 7,024,235 B2 | 4/2006 | Melker et al. |
| 7,027,850 B2 | 4/2006 | Wasserman |
| 7,027,871 B2 | 4/2006 | Burnes et al. |
| 7,033,316 B2 | 4/2006 | Takahashi |
| 7,039,449 B2 | 5/2006 | Al-Ali |
| 7,041,121 B1 | 5/2006 | Williams et al. |
| 7,047,054 B2 | 5/2006 | Benni |
| 7,047,055 B2 | 5/2006 | Boas et al. |
| 7,047,056 B2 | 5/2006 | Hannula et al. |
| 7,048,687 B1 | 5/2006 | Reuss et al. |
| 7,052,509 B2 | 5/2006 | Lennox |
| 7,054,453 B2 | 5/2006 | Causevic et al. |
| 7,054,454 B2 | 5/2006 | Causevic et al. |
| 7,063,669 B2 | 6/2006 | Brawner et al. |
| 7,067,893 B2 | 6/2006 | Mills et al. |
| 7,072,704 B2 | 7/2006 | Bucholz |
| 7,079,036 B2 | 7/2006 | Cooper et al. |
| 7,081,128 B2 | 7/2006 | Hart et al. |
| 7,085,597 B2 | 8/2006 | Fein et al. |
| 7,087,023 B2 | 8/2006 | Daft et al. |
| 7,089,061 B2 | 8/2006 | Grey |
| 7,096,052 B2 | 8/2006 | Mason et al. |
| 7,096,054 B2 | 8/2006 | Abdul-Hafiz et al. |
| 7,097,621 B2 | 8/2006 | Narimatsu et al. |
| 7,107,706 B1 | 9/2006 | Bailey |
| 7,108,659 B2 | 9/2006 | Ross |
| 7,112,196 B2 | 9/2006 | Brosch et al. |
| 7,113,815 B2 | 9/2006 | O'Neil et al. |
| RE39,359 E | 10/2006 | McGraw et al. |
| 7,122,005 B2 | 10/2006 | Shusterman |
| 7,125,383 B2 | 10/2006 | Hoctor et al. |
| 7,127,278 B2 | 10/2006 | Melker et al. |
| 7,132,641 B2 | 11/2006 | Schulz et al. |
| 7,136,452 B2 | 11/2006 | Spartiotis et al. |
| 7,413,305 B2 | 11/2006 | Hajjai et al. |
| 7,158,822 B2 | 1/2007 | Payne, Jr. |
| 7,160,284 B2 | 1/2007 | Ullestad et al. |
| 7,161,484 B2 | 1/2007 | Tsoukalis |
| 7,164,938 B2 | 1/2007 | Geddes et al. |
| 7,167,743 B2 | 1/2007 | Heruth et al. |
| 7,171,251 B2 | 1/2007 | Sarussi et al. |
| 7,179,228 B2 | 2/2007 | Banet |
| 7,181,264 B2 | 2/2007 | Wiesmann et al. |
| 7,181,505 B2 | 2/2007 | Haller et al. |
| 7,190,987 B2 | 3/2007 | Lindekugel |
| 7,192,403 B2 | 3/2007 | Russell et al. |
| 7,197,357 B2 | 3/2007 | Istvan et al. |
| 7,198,605 B2 | 4/2007 | Donofrio et al. |
| 7,204,250 B1 | 4/2007 | Burton |
| 7,214,191 B2 | 5/2007 | Stringer et al. |
| 7,218,232 B2 | 5/2007 | DiSilvestro et al. |
| 7,220,220 B2 | 5/2007 | Stubbs et al. |
| 7,222,624 B2 | 5/2007 | Rashad |
| 7,224,282 B2 | 5/2007 | Terauchi et al. |
| 7,225,007 B2 | 5/2007 | Al-Ali et al. |
| 7,229,400 B2 | 6/2007 | Elliott et al. |
| 7,245,953 B1 | 7/2007 | Parker |
| 7,248,905 B2 | 7/2007 | Fukuda et al. |
| 7,248,910 B2 | 7/2007 | Li et al. |
| 7,254,444 B2 | 8/2007 | Moore et al. |
| 7,255,475 B2 | 8/2007 | Quinn et al. |
| 7,257,448 B2 | 8/2007 | Crowe et al. |
| 7,263,393 B2 | 8/2007 | Smith et al. |
| 7,270,636 B2 | 9/2007 | Lin et al. |
| 7,280,858 B2 | 10/2007 | Al-Ali et al. |
| 7,289,837 B2 | 10/2007 | Mannheimer et al. |
| 7,297,119 B2 | 11/2007 | Westbrook et al. |
| 7,303,680 B2 | 12/2007 | Connell et al. |
| 7,313,427 B2 | 12/2007 | Benni |
| 7,349,726 B2 | 3/2008 | Casciani et al. |
| 7,376,454 B2 | 5/2008 | Casciani et al. |
| 7,415,298 B2 | 8/2008 | Casciani et al. |
| 2001/0000790 A1 | 5/2001 | DeLonzor et al. |
| 2001/0009398 A1 | 7/2001 | Sekura et al. |
| 2002/0013538 A1 | 1/2002 | Teller |
| 2002/0042558 A1 | 4/2002 | Mendelson |
| 2002/0052539 A1 | 5/2002 | Haller et al. |
| 2002/0084904 A1 | 7/2002 | De La Huerga |
| 2002/0091335 A1 | 7/2002 | John et al. |
| 2002/0095092 A1 | 7/2002 | Kondo et al. |
| 2002/0103445 A1 | 8/2002 | Rahdert et al. |
| 2002/0109600 A1 | 8/2002 | Mault et al. |
| 2002/0124295 A1 | 9/2002 | Fenwick et al. |
| 2002/0139368 A1 | 10/2002 | Bachinski |
| 2002/0148470 A1 | 10/2002 | Blue et al. |
| 2002/0151929 A1 | 10/2002 | Goto et al. |
| 2002/0156354 A1 | 10/2002 | Larson |
| 2002/0161309 A1 | 10/2002 | Marro |
| 2002/0173706 A1 | 11/2002 | Takatani et al. |
| 2002/0173708 A1 | 11/2002 | DeLonzor et al. |
| 2003/0004547 A1 | 1/2003 | Owens et al. |
| 2003/0009119 A1 | 1/2003 | Kamm et al. |
| 2003/0009308 A1 | 1/2003 | Kirtley |
| 2003/0018243 A1 | 1/2003 | Gerhardt et al. |
| 2003/0023140 A1 | 1/2003 | Chance |
| 2003/0036685 A1 | 2/2003 | Goodman |
| 2003/0065275 A1 | 4/2003 | Mault et al. |
| 2003/0086156 A1 | 5/2003 | McGuire |
| 2003/0120183 A1 | 6/2003 | Simmons |
| 2003/0122706 A1 | 7/2003 | Choi et al. |
| 2003/0125616 A1 | 7/2003 | Black et al. |
| 2003/0135127 A1 | 7/2003 | Sackner et al. |
| 2003/0144579 A1 | 7/2003 | Buss |
| 2003/0156288 A1 | 8/2003 | Barnum et al. |
| 2003/0176810 A1 | 9/2003 | Maahs et al. |

| Pub. No. | Date | Inventor |
|---|---|---|
| 2003/0189492 A1 | 10/2003 | Harvie |
| 2003/0216728 A1 | 11/2003 | Stern et al. |
| 2003/0225323 A1 | 12/2003 | Kiani et al. |
| 2004/0002655 A1 | 1/2004 | Bolorforosh et al. |
| 2004/0007585 A1 | 1/2004 | Griffith et al. |
| 2004/0030258 A1 | 2/2004 | Williams et al. |
| 2004/0044545 A1 | 3/2004 | Wiesmann et al. |
| 2004/0054287 A1 | 3/2004 | Stephens |
| 2004/0054291 A1 | 3/2004 | Schulz et al. |
| 2004/0064097 A1 | 4/2004 | Peterson |
| 2004/0064165 A1 | 4/2004 | Thompson |
| 2004/0082842 A1 | 4/2004 | Lumba et al. |
| 2004/0092919 A1 | 5/2004 | Ritchie et al. |
| 2004/0100784 A1 | 5/2004 | Willers et al. |
| 2004/0102931 A1 | 5/2004 | Ellis et al. |
| 2004/0116822 A1* | 6/2004 | Lindsey ............. 600/549 |
| 2004/0117891 A1 | 6/2004 | Hannula et al. |
| 2004/0144391 A1 | 7/2004 | Brady et al. |
| 2004/0147974 A1 | 7/2004 | Engmark et al. |
| 2004/0149282 A1 | 8/2004 | Hickle |
| 2004/0163648 A1 | 8/2004 | Burton |
| 2004/0173456 A1 | 9/2004 | Boos et al. |
| 2004/0221370 A1 | 11/2004 | Hannula et al. |
| 2004/0230116 A1 | 11/2004 | Cowan et al. |
| 2004/0231772 A1 | 11/2004 | Leonard et al. |
| 2004/0236207 A1 | 11/2004 | Widener et al. |
| 2004/0236242 A1 | 11/2004 | Graham et al. |
| 2004/0242981 A1 | 12/2004 | Pattisapu |
| 2004/0254490 A1 | 12/2004 | Egli |
| 2004/0254501 A1 | 12/2004 | Mault |
| 2004/0267145 A1 | 12/2004 | David et al. |
| 2005/0001728 A1 | 1/2005 | Applet et al. |
| 2005/0020919 A1 | 1/2005 | Stringer et al. |
| 2005/0027207 A1 | 2/2005 | Westbrook et al. |
| 2005/0029432 A1 | 2/2005 | Bacarella et al. |
| 2005/0041531 A1 | 2/2005 | Sekura et al. |
| 2005/0043599 A1 | 2/2005 | O'Mara |
| 2005/0043763 A1 | 2/2005 | Marcovecchio et al. |
| 2005/0049465 A1 | 3/2005 | Wang |
| 2005/0049501 A1 | 3/2005 | Conero et al. |
| 2005/0059869 A1 | 3/2005 | Scharf et al. |
| 2005/0070776 A1 | 3/2005 | Mannheimer et al. |
| 2005/0070778 A1 | 3/2005 | Lackey et al. |
| 2005/0075550 A1 | 4/2005 | Lindekugel |
| 2005/0080345 A1 | 4/2005 | Finburgh et al. |
| 2005/0085799 A1 | 4/2005 | Luria et al. |
| 2005/0090754 A1 | 4/2005 | Wolff et al. |
| 2005/0096557 A1 | 5/2005 | Vosburgh et al. |
| 2005/0101845 A1 | 5/2005 | Nihtila |
| 2005/0102167 A1 | 5/2005 | Kapoor |
| 2005/0113650 A1 | 5/2005 | Pacione et al. |
| 2005/0113656 A1 | 5/2005 | Chance |
| 2005/0113703 A1 | 5/2005 | Farringdon et al. |
| 2005/0114154 A1 | 5/2005 | Wolkowicz et al. |
| 2005/0171576 A1 | 8/2005 | Williams et al. |
| 2005/0177063 A1* | 8/2005 | Winnie ............. 600/549 |
| 2005/0182458 A1 | 8/2005 | Goedeke |
| 2005/0188991 A1 | 9/2005 | Sun et al. |
| 2005/0190068 A1 | 9/2005 | Gentry et al. |
| 2005/0197548 A1 | 9/2005 | Dietiker |
| 2005/0206518 A1 | 9/2005 | Welch et al. |
| 2005/0215847 A1 | 9/2005 | Heruth et al. |
| 2005/0215880 A1 | 9/2005 | Harrison et al. |
| 2005/0215947 A1 | 9/2005 | Heruth et al. |
| 2005/0216064 A1 | 9/2005 | Heruth et al. |
| 2005/0216199 A1 | 9/2005 | Banet |
| 2005/0222522 A1 | 10/2005 | Heruth et al. |
| 2005/0228234 A1 | 10/2005 | Yang |
| 2005/0228297 A1 | 10/2005 | Banet et al. |
| 2005/0228299 A1 | 10/2005 | Banet et al. |
| 2005/0231686 A1 | 10/2005 | Rathjen |
| 2005/0234312 A1 | 10/2005 | Suzuki et al. |
| 2005/0234317 A1 | 10/2005 | Kiani |
| 2005/0234518 A1 | 10/2005 | Heruth et al. |
| 2005/0240087 A1 | 10/2005 | Keenan et al. |
| 2005/0256523 A1 | 11/2005 | Chen et al. |
| 2005/0261594 A1 | 11/2005 | Banet |
| 2005/0268916 A1 | 12/2005 | Mumford et al. |
| 2005/0277819 A1 | 12/2005 | Kiani et al. |
| 2005/0280531 A1* | 12/2005 | Fadem et al. ............. 340/539.12 |
| 2005/0283082 A1 | 12/2005 | Geddes et al. |
| 2006/0009685 A1 | 1/2006 | Finarov et al. |
| 2006/0009698 A1 | 1/2006 | Banet et al. |
| 2006/0020181 A1 | 1/2006 | Schmidt |
| 2006/0030049 A1 | 2/2006 | Bhimani et al. |
| 2006/0030767 A1 | 2/2006 | Lang et al. |
| 2006/0036137 A1* | 2/2006 | Lewicke ............. 600/301 |
| 2006/0036179 A1 | 2/2006 | Miller |
| 2006/0047447 A1 | 3/2006 | Brady et al. |
| 2006/0058593 A1 | 3/2006 | Drinan et al. |
| 2006/0058690 A1 | 3/2006 | Bartnik et al. |
| 2006/0064133 A1 | 3/2006 | Von Arx et al. |
| 2006/0064134 A1 | 3/2006 | Mazar et al. |
| 2006/0064142 A1 | 3/2006 | Chavan et al. |
| 2006/0064143 A1 | 3/2006 | Von Arx et al. |
| 2006/0074283 A1 | 4/2006 | Henderson et al. |
| 2006/0074324 A1 | 4/2006 | Wu et al. |
| 2006/0084848 A1 | 4/2006 | Mitchnick |
| 2006/0084852 A1 | 4/2006 | Mason et al. |
| 2006/0085227 A1 | 4/2006 | Rosenfeld et al. |
| 2006/0095032 A1 | 5/2006 | Jackson et al. |
| 2006/0100496 A1 | 5/2006 | Avron |
| 2006/0100530 A1 | 5/2006 | Kliot et al. |
| 2006/0100618 A1 | 5/2006 | Chan et al. |
| 2006/0122517 A1 | 6/2006 | Banet et al. |
| 2006/0122520 A1 | 6/2006 | Banet et al. |
| 2006/0124128 A1 | 6/2006 | Deane et al. |
| 2006/0125623 A1 | 6/2006 | Appelt et al. |
| 2006/0132382 A1 | 6/2006 | Jannard |
| 2006/0133362 A1 | 6/2006 | Stein et al. |
| 2006/0142640 A1 | 6/2006 | Takahashi |
| 2006/0149132 A1 | 7/2006 | Iddan |
| 2006/0149339 A1 | 7/2006 | Burnes et al. |
| 2006/0167351 A1 | 7/2006 | Isaacson et al. |
| 2006/0173247 A1 | 8/2006 | Medina |
| 2006/0183980 A1 | 8/2006 | Yang |
| 2006/0184051 A1 | 8/2006 | Hempstead et al. |
| 2006/0189859 A1 | 8/2006 | Kiani et al. |
| 2006/0195026 A1 | 8/2006 | Casciani et al. |
| 2006/0195027 A1 | 8/2006 | Casciani et al. |
| 2006/0195028 A1 | 8/2006 | Hannula et al. |
| 2006/0211929 A1 | 9/2006 | Casciani et al. |
| 2006/0211942 A1 | 9/2006 | Hoctor et al. |
| 2006/0217604 A1 | 9/2006 | Fein et al. |
| 2006/0217605 A1 | 9/2006 | Fein et al. |
| 2006/0217606 A1 | 9/2006 | Fein et al. |
| 2006/0217607 A1 | 9/2006 | Fein et al. |
| 2006/0217608 A1 | 9/2006 | Fein et al. |
| 2006/0224040 A1 | 10/2006 | Khait et al. |
| 2006/0224326 A1 | 10/2006 | St. Ores et al. |
| 2006/0224421 A1 | 10/2006 | St. Ores et al. |
| 2006/0229510 A1 | 10/2006 | Fein et al. |
| 2006/0229511 A1 | 10/2006 | Fein et al. |
| 2006/0241358 A1 | 10/2006 | Al-Ali et al. |
| 2006/0241384 A1 | 10/2006 | Fisher et al. |
| 2006/0241510 A1 | 10/2006 | Halperin et al. |
| 2006/0247504 A1 | 11/2006 | Tice |
| 2006/0253010 A1 | 11/2006 | Brady et al. |
| 2006/0253953 A1 | 11/2006 | Williams |
| 2006/0258922 A1 | 11/2006 | Mason et al. |
| 2006/0264722 A1 | 11/2006 | Hannula et al. |
| 2006/0264723 A1 | 11/2006 | Hannula et al. |
| 2006/0264724 A1 | 11/2006 | Hannula et al. |
| 2006/0264725 A1* | 11/2006 | Hannula et al. ............. 600/340 |
| 2006/0264726 A1 | 11/2006 | Mannheimer et al. |
| 2006/0264727 A1 | 11/2006 | Mannheimer et al. |
| 2006/0264771 A1 | 11/2006 | Lin et al. |
| 2006/0276700 A1 | 12/2006 | O'Neil et al. |
| 2006/0276701 A1 | 12/2006 | Ray |
| 2006/0281984 A1 | 12/2006 | Mannheimer et al. |
| 2007/0032732 A1 | 2/2007 | Shelley et al. |
| 2007/0060808 A1 | 3/2007 | Hoarau |
| 2007/0073117 A1 | 3/2007 | Raridan, Jr. |
| 2007/0073121 A1 | 3/2007 | Hoarau et al. |
| 2007/0073123 A1 | 3/2007 | Raridan, Jr. |
| 2007/0073126 A1 | 3/2007 | Raridan, Jr. |
| 2007/0078316 A1 | 4/2007 | Hoarau |
| 2007/0100218 A1 | 5/2007 | Sweitzer et al. |

| | | | | | |
|---|---|---|---|---|---|
| 2007/0100219 A1 | 5/2007 | Sweitzer et al. | JP | 2000189440 | 7/2000 |
| 2007/0149871 A1 | 6/2007 | Sarussi et al. | JP | 2001161648 | 6/2001 |
| 2007/0208233 A1* | 9/2007 | Kovacs ............ 600/300 | JP | 2001190498 | 7/2001 |
| 2007/0260129 A1 | 11/2007 | Chin et al. | JP | 2001308576 | 11/2001 |
| 2007/0293746 A1 | 12/2007 | Sarussi et al. | JP | 2001332832 | 11/2001 |
| 2008/0009691 A1 | 1/2008 | Parker | JP | 2001346775 | 12/2001 |
| 2008/0076988 A1 | 3/2008 | Sarussi et al. | JP | 2002065647 | 3/2002 |
| 2008/0076990 A1 | 3/2008 | Sarussi et al. | JP | 2003210402 | 7/2003 |
| 2008/0081967 A1 | 4/2008 | Andersohn et al. | JP | 2003235813 | 8/2003 |
| 2008/0139908 A1 | 6/2008 | Kurth | JP | 2003265425 | 9/2003 |
| 2008/0143080 A1 | 6/2008 | Burr | JP | 2004016659 | 1/2004 |
| 2008/0146890 A1 | 6/2008 | LeBoeuf et al. | JP | 2004065832 | 3/2004 |
| 2008/0165017 A1 | 7/2008 | Schwartz | JP | 2004121549 | 4/2004 |
| 2008/0177163 A1 | 7/2008 | Wang et al. | JP | 2004258761 | 9/2004 |
| 2008/0221413 A1 | 9/2008 | Hoarau | JP | 2005013612 | 1/2005 |
| 2008/0221414 A1 | 9/2008 | Baker | JP | 2005110816 | 4/2005 |
| 2008/0228053 A1 | 9/2008 | Wang et al. | JP | 2005111187 | 4/2005 |
| 2008/0230363 A1 | 9/2008 | Yang et al. | JP | 2005143782 | 6/2005 |
| | | | JP | 2005168600 | 6/2005 |

FOREIGN PATENT DOCUMENTS

| | | | | | |
|---|---|---|---|---|---|
| | | | JP | 2005266860 | 9/2005 |
| CN | 1657007 | 8/2005 | JP | 2006061178 | 3/2006 |
| DE | 3705493 | 8/1988 | JP | 2006066512 | 3/2006 |
| DE | 3744781 | 1/1989 | JP | 2006122693 | 5/2006 |
| DE | 3810411 | 10/1989 | KR | 2003065871 | 5/2004 |
| DE | 3927038 | 2/1991 | KR | 2005106928 | 12/2004 |
| DE | 4429845 | 10/1995 | RU | 2132204 | 6/1999 |
| DE | 19541605 | 5/1997 | WO | WO9001293 | 2/1990 |
| DE | 19939302 | 5/2001 | WO | WO9111137 | 8/1991 |
| DE | 10029205 | 1/2002 | WO | WO9115151 | 10/1991 |
| EP | 268850 | 6/1988 | WO | WO9118550 | 12/1991 |
| EP | 0313238 | 4/1989 | WO | WO9220273 | 11/1992 |
| EP | 338518 | 10/1989 | WO | WO9506430 | 3/1995 |
| EP | 463620 | 1/1992 | WO | WO9512349 | 5/1995 |
| EP | 543172 | 5/1993 | WO | WO9615714 | 5/1996 |
| EP | 0572684 | 12/1993 | WO | WO9616591 | 6/1996 |
| EP | 0573137 | 12/1993 | WO | WO9641138 | 12/1996 |
| EP | 578530 | 1/1994 | WO | WO9720494 | 6/1997 |
| EP | 580385 | 1/1994 | WO | WO9720497 | 6/1997 |
| EP | 775311 | 8/1994 | WO | WO9817174 | 4/1998 |
| EP | 621026 | 10/1994 | WO | WO9947039 | 9/1999 |
| EP | 0631756 | 1/1995 | WO | WO0059374 | 10/2000 |
| EP | 665025 | 8/1995 | WO | WO0078209 | 12/2000 |
| EP | 0695139 | 2/1996 | WO | WO0101855 | 1/2001 |
| EP | 0721110 | 7/1996 | WO | WO0117425 | 3/2001 |
| EP | 1048323 | 2/2000 | WO | WO0176471 | 10/2001 |
| EP | 996063 | 4/2000 | WO | WO0187224 | 11/2001 |
| EP | 1130412 | 5/2001 | WO | WO0215784 | 2/2002 |
| EP | 1169965 | 1/2002 | WO | WO02065901 | 8/2002 |
| EP | 1683478 | 7/2006 | WO | WO02066977 | 8/2002 |
| EP | 1945099 | 7/2008 | WO | WO02/089664 | 11/2002 |
| FR | 2555744 | 11/1983 | WO | WO03026558 | 4/2003 |
| FR | 2601137 | 1/1988 | WO | WO03057030 | 7/2003 |
| GB | 834469 | 5/1960 | WO | WO03071928 | 9/2003 |
| GB | 2135074 | 8/1984 | WO | WO03080152 | 10/2003 |
| GB | 2390903 | 1/2004 | WO | WO2004030480 | 4/2004 |
| JP | 55024614 | 2/1980 | WO | WO2004046673 | 6/2004 |
| JP | 04057161 | 2/1992 | WO | WO2004084720 | 10/2004 |
| JP | 07336597 | 12/1995 | WO | WO2005046466 | 5/2005 |
| JP | 08111295 | 4/1996 | WO | WO2005079663 | 9/2005 |
| JP | 08112257 | 5/1996 | WO | WO2006007231 | 1/2006 |
| JP | 08336546 | 12/1996 | WO | WO2006017117 | 2/2006 |
| JP | O9010319 | 1/1997 | WO | WO2006021956 | 3/2006 |
| JP | 09154937 | 6/1997 | WO | WO2006094108 | 9/2006 |
| JP | 10314149 | 12/1998 | WO | WO2007048039 | 4/2007 |
| JP | 11259583 | 9/1999 | | | |

* cited by examiner

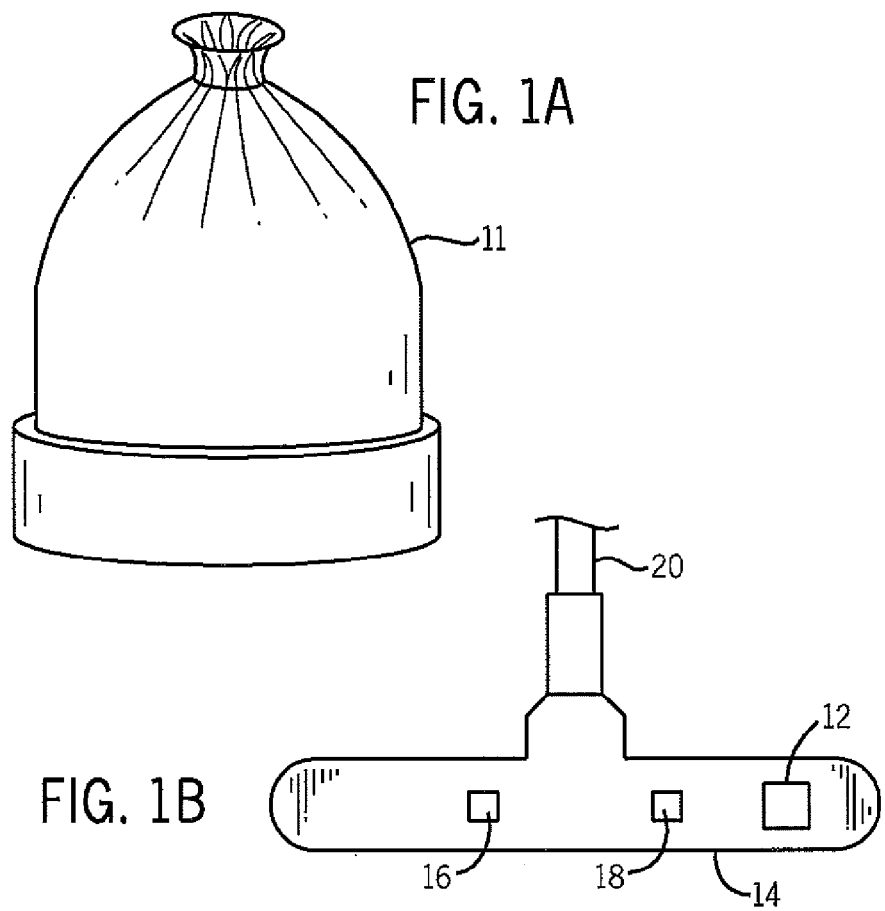
FIG. 1A
FIG. 1B
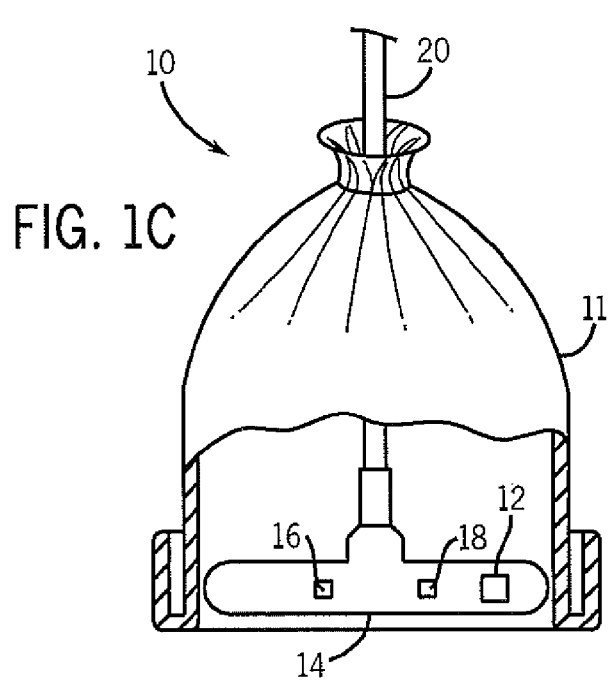
FIG. 1C

# MEDICAL SENSOR AND TECHNIQUE FOR USING THE SAME

BACKGROUND

The present disclosure relates generally to medical devices and, more particularly, to sensors used for sensing physiological parameters of a patient.

In the field of medicine, doctors often desire to monitor certain physiological characteristics of their patients. Accordingly, a wide variety of devices have been developed for monitoring many such physiological characteristics. Such devices provide doctors and other healthcare personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered. More specifically, the light passed through the tissue is typically selected to be of one or more wavelengths that may be absorbed or scattered by the blood in an amount correlative to the amount of the blood constituent present in the blood. The amount of light absorbed and/or scattered may then be used to estimate the amount of blood constituent in the tissue using various algorithms.

Pulse oximetry readings involve placement of a sensor on a patient's tissue, typically via a lightly adhesive sensor, a clip-style sensor, or a sensor that may be fitted into a wearable garment, such as a hat. In certain medical environments, placement of such sensors on the tissue may preclude the placement of other sensors for measuring parameters of interest.

BRIEF DESCRIPTION OF THE DRAWINGS

Advantages of the disclosure may become apparent upon reading the following detailed description and upon reference to the drawings in which:

FIG. 1A illustrates a perspective view of an exemplary hat structure for holding a pulse oximetry sensor on a patient's tissue;

FIG. 1B illustrates a perspective view of an exemplary pulse oximetry sensor body with an integrated temperature sensor that may be incorporated with the hat of FIG. 1A;

FIG. 1C illustrates a perspective view of the hat of FIG. 1A with the pulse oximetry sensor with an integrated temperature sensor of FIG. 1B;

DETAILED DESCRIPTION OF SPECIFIC EMBODIMENTS

Figure 2A:
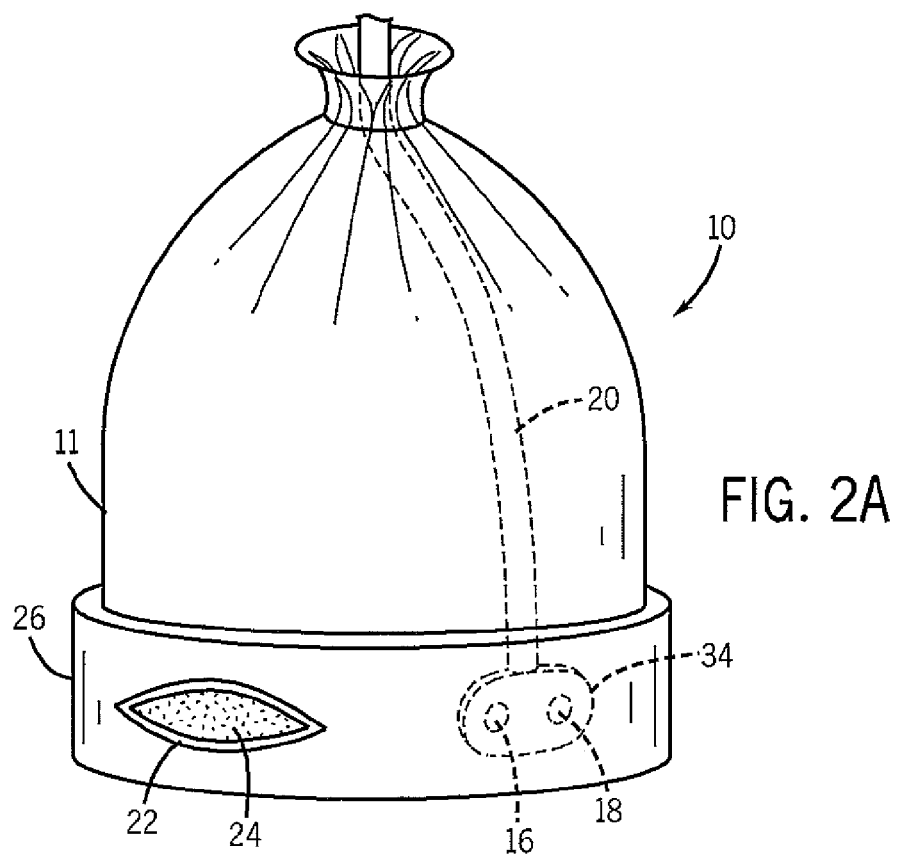
FIG. 2A illustrates a perspective view of an exemplary hat pulse oximetry sensor with a temperature-sensitive film incorporated into the band of the hat.

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Sensors for pulse oximetry or other applications utilizing spectrophotometry are provided therein that include temperature sensing capabilities. In an embodiment, a hat-based pulse oximetry sensor assembly for neonatal patients may include a temperature sensor. Such a sensor assembly may provide certain advantages for caregivers. In one embodiment, applying a hat-based sensor that is easy to pull on and off of a baby's head saves time for the caregiver. Because many medical parameters may be monitored in one neonatal patient, combining their sensing capabilities into one sensor assembly eliminates the time involved in applying multiple sensors to the patient. In another embodiment, the parents of an infant in the intensive care unit may prefer having fewer visible sensors on the infant. A hat-based sensor may effectively hide a pulse oximetry sensor as well as a temperature sensor.

In an embodiment, an oximetry sensor with an integral temperature transducer may be adapted for placement in a hat (for example, a neonatal stocking cap), a headband, or other wearable structure (i.e. a glove, a sock, a wristband) to apply the sensor on the body of the user. FIGS. 1A-1C illustrate an assembly drawing of an embodiment of a sensor assembly 10 including a wearable structure, which may be a hat 11, as shown in FIG. 1A. A reflectance-type pulse oximetry sensor 15, as shown in FIG. 1B, is adapted to be placed or adhered to the inside of a hat 11.

The sensor 15 includes a substrate 14 that may be made from any suitable material. In an embodiment, the substrate 14 is a foam or other conformable material. In one embodiment, the substrate 14 is black or dark in color to absorb stray light and minimize any shunting of light between sensor and patient skin. In one embodiment, the substrate 14 may include an adhesive material to secure the sensor directly to the tissue. In one embodiment, the sensor 15 may include an emitter 16 containing emitters for two or more wavelengths of lights and a detector 18 spaced apart from the emitter 16. The sensor 15 also includes a temperature sensor 12 adapted to provide an indication of the tissue temperature.

Also shown in FIG. 1B is a cable 20 for providing drive current to the temperature sensor 12, providing the temperature signal to a downstream medical device, providing drive current to the LED, and providing the detector signal to the medical device. In addition to providing the electrical connection to the downstream medical device, the cable may provide shielding to protect the small signals from the detector against external electrical interference. In addition, the sensor 15 may include suitable structures for providing electrical connections to the cable and/or downstream medical device, such as a flex circuit, a Faraday shield, and leads connecting the optical components and the temperature transducer of the sensor 15 to the electrical components.

The sensor assembly 10 is shown fully assembled in FIG. 1C. As shown, the sensor 15 is positioned on the interior of the hat 11 such that the emitter 16 and detector 18, as well as the temperature sensor 12, may come into contact with the skin when the sensor assembly 10 is applied to a patient. The sensor 15 may be attached (e.g., adhered or sewn into) to the inside band of a hat. In one embodiment, the hat may include indicators to position the sensor 15 on a particular location on the patient's forehead, for example to position the sensor 15 on the lower forehead region, above the eyebrow, with the sensor optics (emitter 16 and detector 18) located above and predominantly lateral to or centered over the iris. The location of the reflectance sensor 15 in the hat allows appropriate placement of the sensor in the desired forehead location by a user not skilled in sensor placement. FIG. 1C shows that the cable 20 is positioned through a hole in the top of the hat 11. In an embodiment, the cable 20 may be adhered or otherwise constrained in the hat 11 so that the cable generally is positioned away from the sensor 15 to avoid interfering with the patient's eyesight or bothering the patient.

Figure 2B:
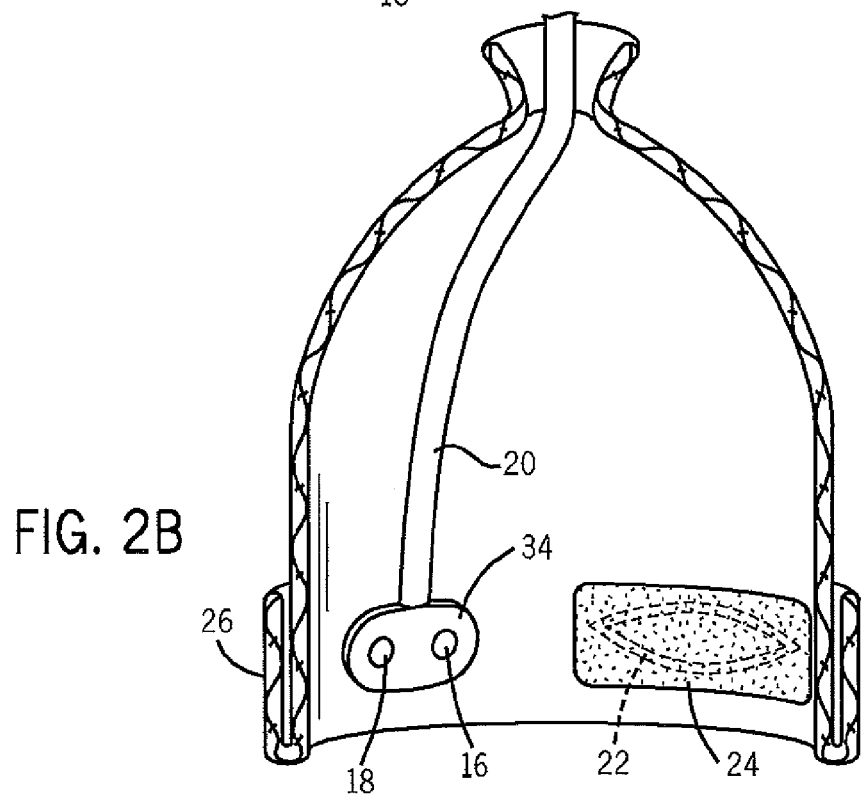
FIG. 2B is a cross-sectional view of the exemplary hat pulse oximetry sensor of FIG. 2A.

In certain embodiments, it is envisioned that temperature data generated from the temperature sensor 12 may be further processed by a downstream monitor to be stored or to generate displays or other information related to the patient's temperature. However, as patients may not be familiar with the medical monitor icons and displays that may be used in conjunction with a sensor assembly 10, in certain embodiments it may be advantageous to provide a sensor assembly 10 with a temperature-sensitive signal that is easily identifiable by a patient. FIG. 2A illustrates a sensor assembly 10 that may be applied to a patient's head. The sensor assembly 10 includes a hat 11 and a medical sensor 34 (e.g., a pulse oximetry sensor) including an emitter 16, a detector 18, and a cable 20. The pulse oximetry sensor 34 is placed on the interior of the hat band 26. The sensor assembly 10 also includes a temperature-sensitive film 24 where the color of the film 24 is an indication of the patient's temperature. The temperature-sensitive film 24 may be viewed by the patient or the caregiver through a viewing window, depicted here as a buttonhole 22 formed in the knit fabric of the hat 11. As shown in FIG. 2B, the temperature-sensitive film 24 may be located on the interior of the hat band 26 at approximately the same latitude as the pulse oximetry sensor 34. In one embodiment, the temperature-sensitive film 24 may be Clinitemp thermometer, available from Liquid. Crystal Resources LLC (Glenview, Ill.), which includes a moving line along a temperature scale that allows a caregiver to view a temperature reading. In one embodiment, the sensor assembly 10 may also include a reference color strip that may be compared to the color of the temperature-sensitive film 24. When the color matches or is brighter than the color in the reference color strip, a patient or caregiver may be alerted to a change in temperature.

Figure 3A:
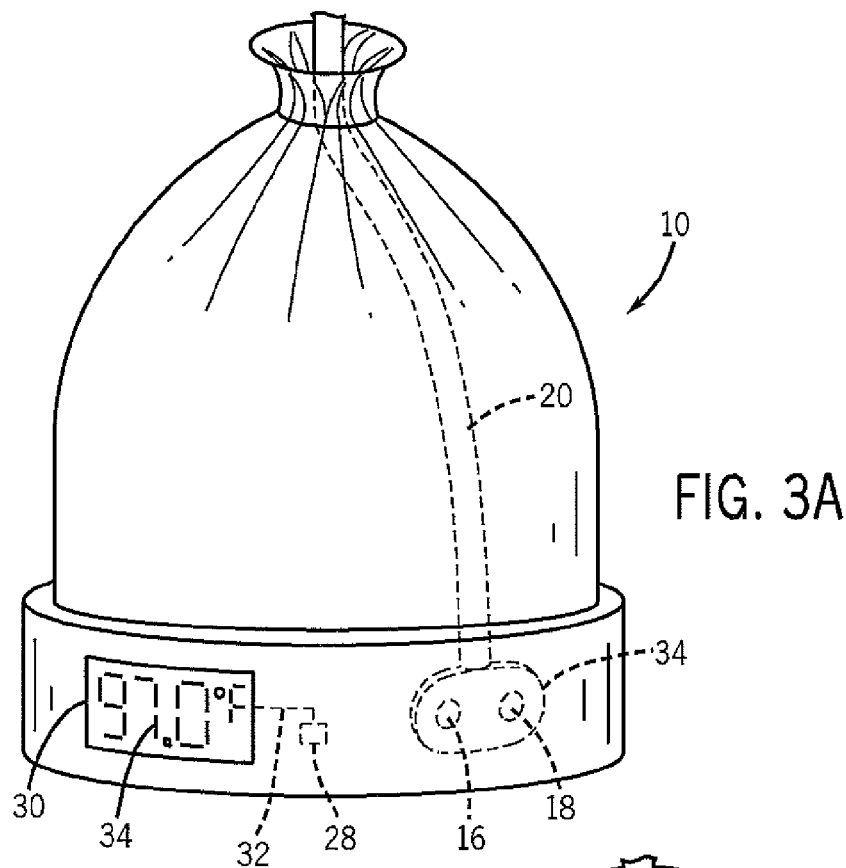
FIG. 3A illustrates an exemplary hat pulse oximetry sensor with an integrated temperature display.
Figure 3B:
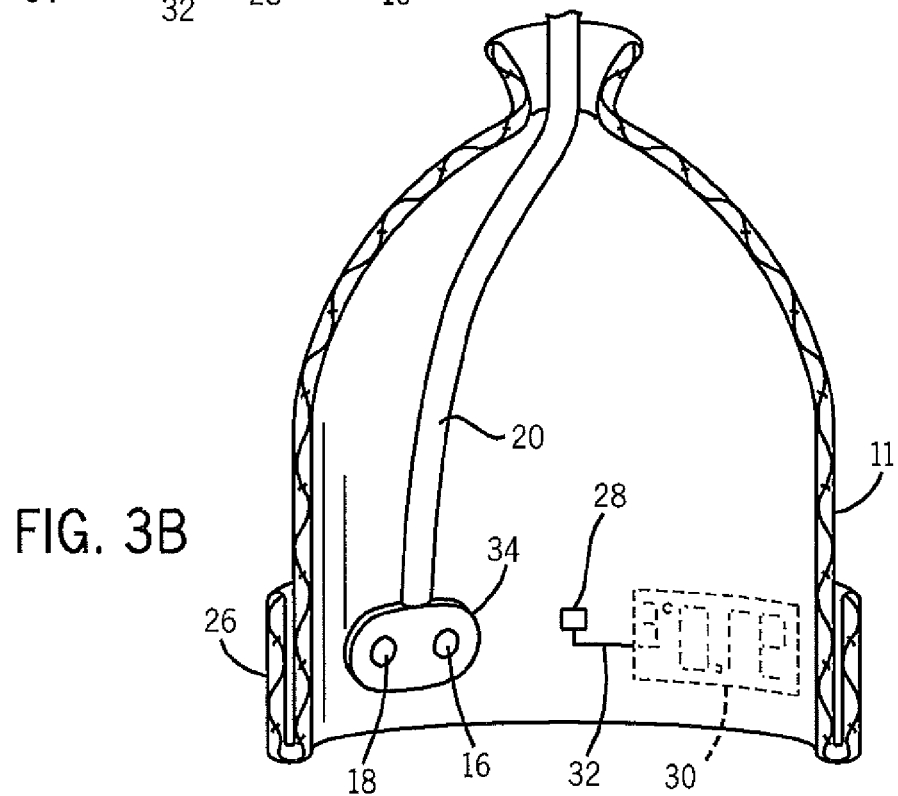
FIG. 3B is a cross-sectional view of the exemplary hat pulse oximetry sensor of FIG. 3A.

In one embodiment, a wearable sensor assembly may include an integral digital display for displaying patient temperature readings. FIG. 3A shows an embodiment of a hat-based sensor assembly 10 for pulse oximetry or other medical monitoring that includes a temperature sensor 12 connected by lead 32 to an integral display 30. The display 30 may be any suitable display, such as an LCD screen. As shown in FIG. 3B, the medical sensor 34 and temperature sensor 12 are located on the inside of the hat band to directly contact the forehead tissue when the hat is put on a patient's head. Such an embodiment may allow healthcare workers to quickly spot changes in patient temperature. For example, a quick glance at a digital display may alert a healthcare worker to check the patient's status or take steps to address the patient's temperature.

Figure 4:
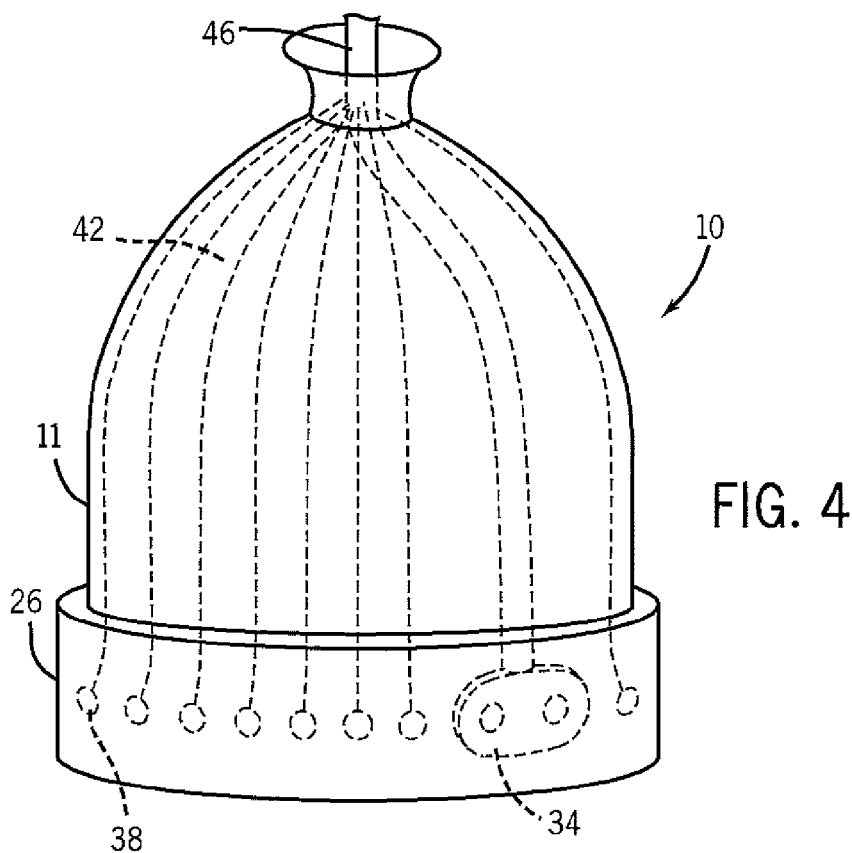
FIG. 4 illustrates an exemplary hat pulse oximetry sensor with an array of temperature sensors woven into the fabric of the hat.

FIG. 4 shows a hat-based sensor assembly 10 that includes an array of temperature sensors 38 that may located on or in the fabric of the hat 11. The temperature sensors 38 may be connected by leads 42 to cable 20, which may also carry signals to and from the an emitter 16 and detector 18 of medical sensor 34. In one embodiment, the temperature sensors 38 may be woven into the fabric of the hat 11.

Figure 5:
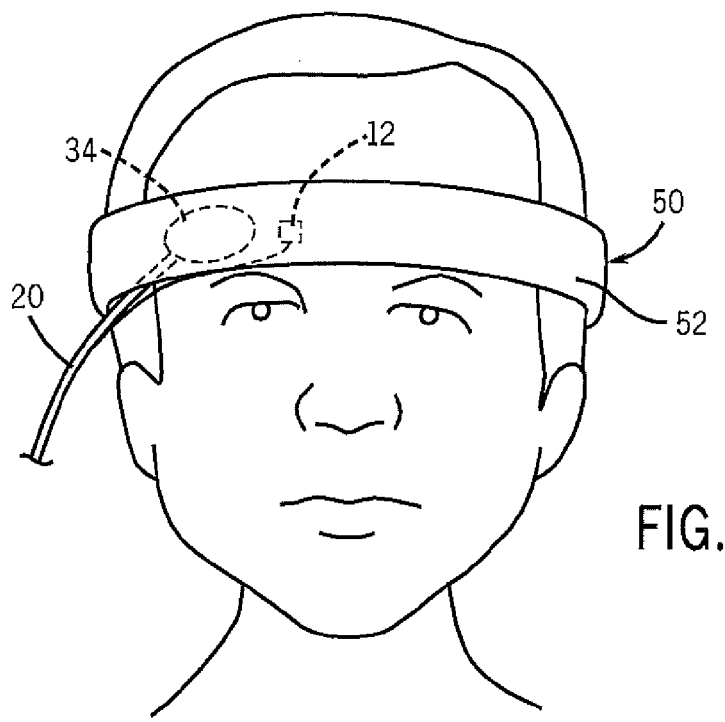
FIG. 5 illustrates a perspective view of an exemplary headband-style sensor with a temperature sensor.

FIG. 5 illustrates an embodiment of a headband-based sensor assembly 50 that includes a medical sensor 34 and a temperature sensor 12. The headband-based sensor assembly 50 may include a strap or band 52 that may be fitted around a patient's forehead tissue to contact the sensor 34 with the tissue. In certain embodiments, a temperature sensor 12 may send feedback to a downstream monitor through cable 20 relating to both the medical sensor and the temperature sensor 12

Figure 6:
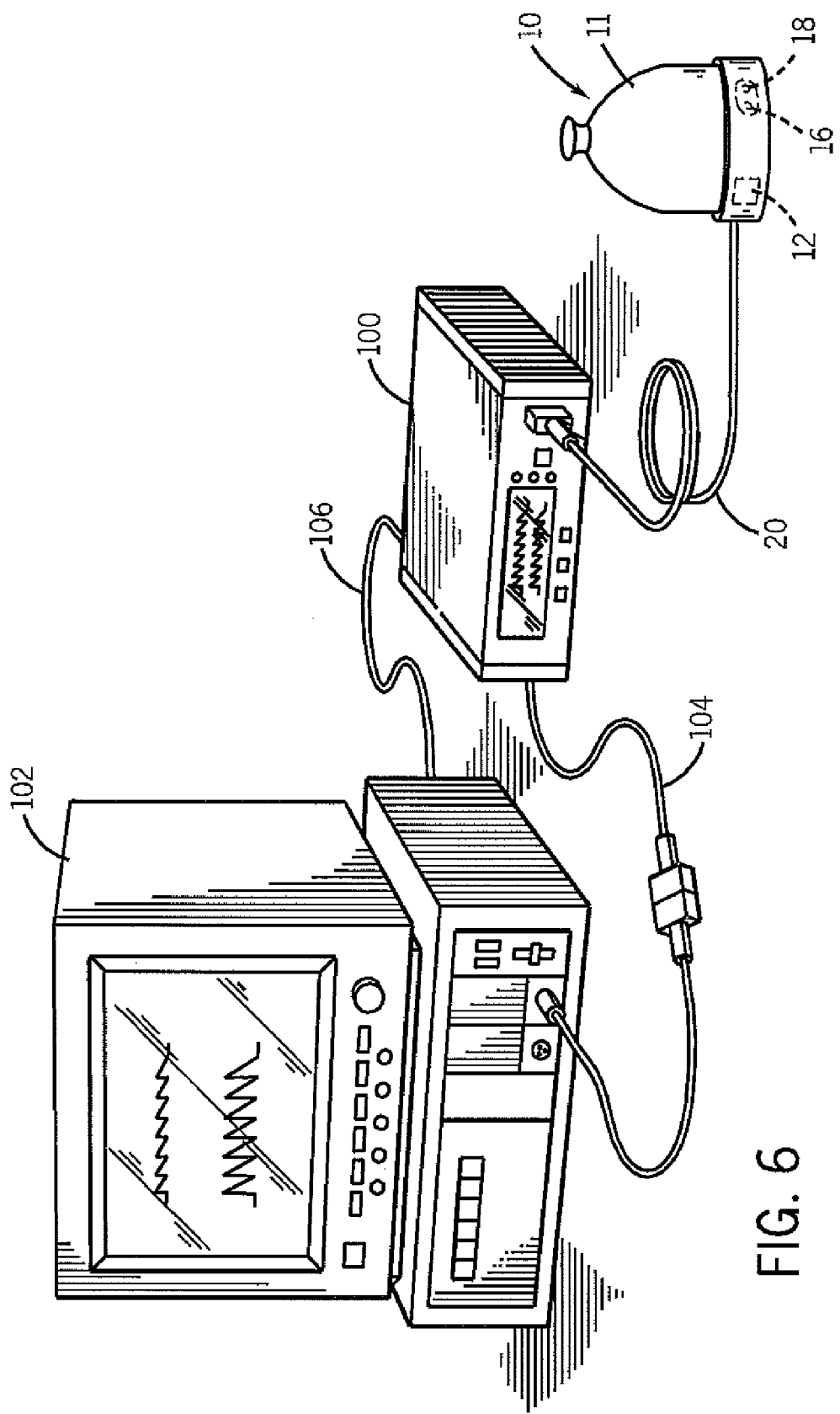
FIG. 6 illustrates an exemplary pulse oximetry system coupled to a multi-parameter patient monitor and a sensor.

A sensor or sensor assembly, illustrated generically as a sensor assembly 10, may be used in conjunction with a pulse oximetry monitor 100, as illustrated in FIG. 6. It should be appreciated that the cable 20 of the sensor assembly 10 may be coupled to the monitor 100 or it may be coupled to a transmission device to facilitate wireless transmission between the sensor assembly 10 and the monitor 100. The monitor 100 may be any suitable pulse oximeter, such as those available from Nellcor Puritan Bennett LLC. Furthermore, to upgrade conventional pulse oximetry provided by the monitor 100 to provide additional functions, the monitor 100 may be coupled to a multi-parameter patient monitor 102 via a cable 104 connected to a sensor input port or via a cable 106 connected to a digital communication port.

Figure 7:
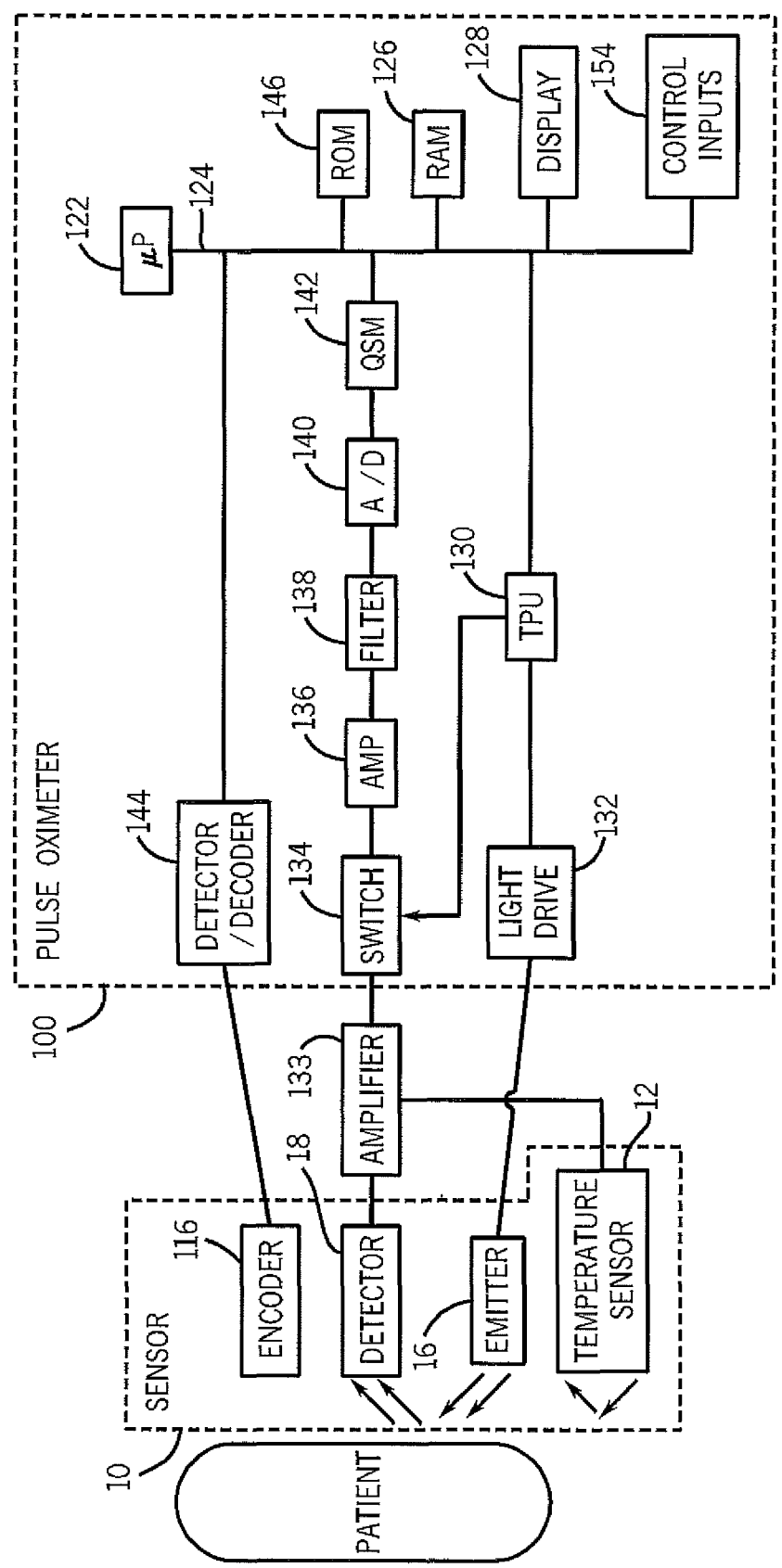
FIG. 7 is a block diagram of an exemplary pulse oximetry system.

FIG. 7 is a block diagram of an embodiment of a pulse oximeter 100 that may be configured to implement the embodiments of the present disclosure. Light from emitter 16 may pass into a blood perfused tissue, and may be scattered, and then detected by detector 18. A sensor assembly 10 containing an emitter 16 and a detector 18 may also contain an encoder 116 which may be capable of providing signals indicative of the wavelength(s) of light source 16 to allow the oximeter to select appropriate calibration coefficients for calculating oxygen saturation. The encoder 116 may, in an embodiment, be a resistor. In an embodiment, the sensor assembly 10 also includes a temperature sensor/transducer 12 and may be capable of carrying a signal from the temperature sensor 12 to a monitor 100.

In an embodiment, the sensor assembly 10 may be connected to a pulse oximetry monitor 100. The monitor 100 may include a microprocessor 122 coupled to an internal bus 124. Also connected to the bus may be a RAM memory 126 and a display 128. A time processing unit (TPU) 130 may provide timing control signals to light drive circuitry 132, which controls when the emitter 16 is activated, and if multiple light sources are used, the multiplexed timing for the different light sources. TPU 130 may also control the gating-in of signals from detector 18 through an amplifier 133 and a switching circuit 134. These signals are sampled at the proper time, depending at least in part upon which of multiple light sources is activated, if multiple light sources are used. The received signal from the detector 18 and the temperature sensor 12 may be passed through an amplifier 136, a low pass filter 138, and an analog-to-digital converter 140. The digital data may then be stored in a queued serial module (QSM) 142, for later downloading to RAM 126 as QSM 142 fills up. In an embodiment, there may be multiple parallel paths of separate amplifier, filter, and A/D converters for multiple light wavelengths or spectra received and/or the temperature data from the temperature sensor 12. In one embodiment, the signal from the temperature sensor 12 may have its own data path and may be processed separately from the signal from the detector 18.

In an embodiment, the monitor 100 may be configured to receive signals from the sensor assembly 10. In certain embodiments, the signals may be related to a temperature sensor 12 and may be processed by the monitor 100 to indicate the patient's temperature and/or whether it is too high or too low. The monitor 100 may be configured to provide an indication about the sensor condition, such as an audio alarm, visual alarm or a display message if the patient's temperature is outside of a predetermined range. Further, the monitor 100 may be configured to receive information about the temperature sensor 12 from a memory chip or other device, such as the encoder 116, which may be on the sensor assembly 10 or the cable 20. In an embodiment, such a device may include a code or other identification parameter that may allow the monitor 100 to select an appropriate software or hardware instruction for processing the signal. In an embodiment, a monitor 100 may run an algorithm or code for processing the signal provided by the temperature sensor 12. In one embodiment, when the encoder 116 indicates that the sensor assembly 10 is configured for neonates, the temperature range that is indicative of acceptable temperatures may be slightly narrower than in sensors designed for adult populations.

The temperature sensor 12 may include one or more temperature-sensing structures that contact the tissue of the patient. The temperature sensor 12 may be any suitable medical-grade temperature sensor, such as resistance-based temperature sensors and infrared temperature sensors available from Thermometrics (Plainville, Conn.).

In an embodiment, based at least in part upon the received signals corresponding to the light received by detector 18, microprocessor 122 may calculate the oxygen saturation using various algorithms. These algorithms may require coefficients, which may be empirically determined, and may correspond to the wavelengths of light used. The algorithms may be stored in a ROM 146 and accessed and operated according to microprocessor 122 instructions.

In an embodiment of a two-wavelength system, the particular set of coefficients chosen for any pair of wavelength spectra may be determined by a value indicated by the encoder 116 corresponding to a particular light source in a particular sensor assembly 10. In one embodiment, multiple resistor values may be assigned to select different sets of coefficients. In another embodiment, the same resistors are used to select from among the coefficients appropriate for an infrared source paired with either a near red source or far red source. The selection between whether the near red or far red set will be chosen can be selected with a control input from control inputs 154. Control inputs 154 may be, for instance, a switch on the pulse oximeter, a keyboard, or a port providing instructions from a remote host computer. Furthermore, any number of methods or algorithms may be used to determine a patient's pulse rate, oxygen saturation or any other desired physiological parameter.

The sensor assembly 10 includes an emitter 16 and a detector 18 that may be of any suitable type. For example, the emitter 16 may be one or more light emitting diodes adapted to transmit one or more wavelengths of light in the red to infrared range, and the detector 18 may one or more photodetectors selected to receive light in the range or ranges emitted from the emitter 16. Alternatively, an emitter 16 may also be a laser diode or a vertical cavity surface emitting laser (VCSEL). An emitter 16 and detector 18 may also include optical fiber sensing elements. An emitter 16 may include a broadband or "white light" source, in which case the detector could include any of a variety of elements for selecting specific wavelengths, such as reflective or refractive elements or interferometers. These kinds of emitters and/or detectors would typically be coupled to the rigid or rigidified sensor via fiber optics. Alternatively, a sensor assembly 10 may sense light detected from the tissue is at a different wavelength from the light emitted into the tissue. Such sensors may be adapted to sense fluorescence, phosphorescence, Raman scattering, Rayleigh scattering and multi-photon events or photoacoustic effects.

For pulse oximetry applications using either transmission or reflectance type sensors the oxygen saturation of the patient's arterial blood may be determined using two or more wavelengths of light, most commonly red and near infrared wavelengths. Similarly, in other applications, a tissue water fraction (or other body fluid related metric) or a concentration of one or more biochemical components in an aqueous environment may be measured using two or more wavelengths of light, most commonly near infrared wavelengths between about 1,000 nm to about 2,500 nm. It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible ultraviolet, or X-ray spectra.

The emitter 16 and the detector 18, and in some embodiments the temperature sensor 12, may be disposed on a sensor body, which may be made of any suitable material, such as plastic, foam, woven material, or paper. Alternatively, the emitter 16 and the detector 18 may be remotely located and optically coupled to the sensor assembly 10 using optical fibers. In the depicted embodiments, the sensor assembly 10 is coupled to a cable that is responsible for transmitting electrical and/or optical signals to and from the emitter 16 and detector 18 of the sensor assembly 10. The cable may be permanently coupled to the sensor assembly 10, or it may be removably coupled to the sensor assembly 10—the latter alternative being more useful and cost efficient in situations where the sensor assembly 10 is disposable.

The sensor assembly 10 may be a "transmission type" sensor. Transmission type sensors include an emitter 16 and detector 18 that are typically placed on opposing sides of the sensor site. If the sensor site is a fingertip, for example, the sensor assembly 10 is positioned over the patient's fingertip such that the emitter 16 and detector 18 lie on either side of the patient's nail bed. In other words, the sensor assembly 10 is positioned so that the emitter 16 is located on the patient's fingernail and the detector 18 is located 180° opposite the emitter 16 on the patient's finger pad. During operation, the emitter 16 shines one or more wavelengths of light through the patient's fingertip and the light received by the detector 18 is processed to determine various physiological characteristics of the patient. In each of the embodiments discussed herein, it should be understood that the locations of the emitter 16 and the detector 18 may be exchanged. For example, the detector 18 may be located at the top of the finger and the emitter 16 may be located underneath the finger. In either arrangement, the sensor assembly 10 will perform in substantially the same manner.

Reflectance type sensors also operate by emitting light into the tissue and detecting the light that is transmitted and scattered by the tissue. However, reflectance type sensors include an emitter 16 and detector 18 that are typically placed on the same side of the sensor site. For example, a reflectance type sensor may be placed on a patient's fingertip or forehead such that the emitter 16 and detector 18 lie side-by-side. Reflectance type sensors detect light photons that are scattered back to the detector 18. A sensor assembly 10 may also be a "transflectance" sensor, such as a sensor that may subtend a portion of a baby's heel.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of blood oxygen saturation, but these techniques may also be utilized for the measurement and/or analysis of other blood constituents. For example, using the same, different, or additional wavelengths, the present techniques may be utilized for the measurement and/or analysis of carboxyhemoglobin, met-hemoglobin, total hemoglobin, fractional hemoglobin, intravascular dyes, and/or water content. Rather, the various embodiments may cover all modifications, equivalents, and alternatives falling within the spirit and scope of the disclosure as defined by the following appended claims

What is claimed is:

1. An apparatus comprising:
a stocking cap capable of being applied to a patient's head;
a substrate disposed adjacent the stocking cap;
a pulse oximetry sensor disposed on the substrate, wherein the pulse oximetry sensor comprises a light emitter and a light detector;
a cable disposed on the substrate, wherein the cable extends from the substrate through an open portion of the stocking cap configured to be proximate to a top of the stocking cap when the stocking cap is applied to the patient; and
an array of temperature sensors woven into the stocking cap, wherein each of the array of temperature sensors is capable of providing a feedback related to a temperature of the patient.

2. The apparatus, as set forth in claim 1, wherein the feedback comprises an electrical signal.

3. The apparatus, as set forth in claim 1, wherein each of the array of temperature sensors comprises a transducer.

4. The apparatus, as set forth in claim 1, wherein each of the array of temperature sensors comprises a colorimetric film.

5. The apparatus, as set forth in claim 1, wherein each of the array of temperature sensors is disposed on the substrate.

6. The apparatus of claim 1, wherein the stocking cap comprises a stocking cap capable of being placed on the head of a neonate.

7. The apparatus, as set forth in claim 1, wherein the cable is electrically connected to the pulse oximetry sensor and the temperature sensor.

8. The apparatus, as set forth in claim 1, comprising a digital LCD display disposed on the stocking cap configured to display the temperature of the patient.

9. A pulse oximetry system comprising:
a pulse oximetry monitor; and
a sensor assembly capable of being operatively coupled to the pulse oximetry monitor, the sensor assembly comprising:
a stocking cap capable of being applied to a patient's head;
a substrate disposed on the stocking cap;
a pulse oximetry sensor disposed on the substrate, wherein the pulse oximetry sensor comprises a light emitter and a light detector;
a cable disposed on the substrate, wherein the cable extends from the substrate generally through the stocking cap and configured to be generally proximate to a top of the stocking cap when the stocking cap is applied to the patient; and
an array of temperature sensors woven into the stocking cap, wherein each of the array of temperature sensors is capable of providing a feedback to the pulse oximetry monitor.

10. The system, as set forth in claim 9, wherein each of the array of temperature sensors comprises a transducer.

11. The system, as set forth in claim 9, wherein each of the array of temperature sensors comprises a colorimetric film.

12. The system, as set forth in claim 9, wherein each of the array of temperature sensors is disposed on the substrate.

13. The system, as set forth in claim 9, wherein the stocking cap comprises a stocking cap capable of being placed on the head of a neonate.

14. A sensor comprising:
a structure capable of being applied to a patient's head;
a substrate disposed on the structure;
a pulse oximetry sensor disposed on the substrate, wherein the pulse oximetry sensor comprises a light emitter and a light detector;
an array of temperature sensors woven into the structure, wherein each of the array of temperature sensors is capable of providing a feedback related to a temperature of the patient; and
a cable disposed on the substrate, wherein the cable is electrically connected to the pulse oximetry sensor and each of the array of temperature sensors.

15. The sensor, as set forth in claim 14, wherein each of the array of temperature sensors comprises a transducer.

16. The sensor, as set forth in claim 14, wherein each of the array of temperature sensors comprises a colorimetric film.

17. The sensor, as set forth in claim 14, wherein each of the array of temperature sensors is disposed on the substrate.

18. The sensor, as set forth in claim 14, wherein the structure comprises a stocking cap.

19. The sensor, as set forth in claim 14, wherein the structure comprises a headband.

* * * * *